United States Patent
Kusakabe (10) Patent No.: US 9,262,591 B2
(45) Date of Patent: Feb. 16, 2016

(54) ELECTRONIC STATE COMPUTING METHOD, ELECTRONIC STATE COMPUTING DEVICE, AND RECORDING MEDIUM

(75) Inventor: Koichi Kusakabe, Suita (JP)

(73) Assignee: Osaka University, Osaka (JP)

( * ) Notice: Subject to any disclaimer, the term of this patent is extended or adjusted under 35 U.S.C. 154(b) by 690 days.

(21) Appl. No.: 13/061,661

(22) PCT Filed: Aug. 28, 2009

(86) PCT No.: PCT/JP2009/004219
§ 371 (c)(1),
(2), (4) Date: Mar. 31, 2011

(87) PCT Pub. No.: WO2010/023943
PCT Pub. Date: Mar. 4, 2010

(65) Prior Publication Data
US 2011/0191077 A1    Aug. 4, 2011

(30) Foreign Application Priority Data
Sep. 1, 2008 (JP) ................................ 2008-223813

(51) Int. Cl.
*G06F 7/60* (2006.01)
*G06F 17/10* (2006.01)
(Continued)

(52) U.S. Cl.
CPC ............. *G06F 19/701* (2013.01); *G06F 17/10* (2013.01); *G06F 17/13* (2013.01); *G06F 17/5009* (2013.01); *G06F 19/16* (2013.01)

(58) Field of Classification Search
CPC ....... G06F 17/5009; G06F 17/10; G06F 17/13; G06F 19/16
USPC ..................................................... 703/2, 22, 5
See application file for complete search history.

(56) References Cited

U.S. PATENT DOCUMENTS 7,689,367 B2 * 3/2010 Mills ............................... 702/22
2006/0138397 A1 * 6/2006 Mattis ............................ 257/15
(Continued)

FOREIGN PATENT DOCUMENTS

JP     2006/196908 A1    7/2006
JP     2006/277582 A1   10/2006
(Continued)

OTHER PUBLICATIONS

Robert van Leeuwen, NPL, "Kohn-Sham potentials in density functional theory", Oct. 18, 1994.*
(Continued)

*Primary Examiner* — Omar Fernandez Rivas
*Assistant Examiner* — Angel Calle
(74) *Attorney, Agent, or Firm* — Muncy, Geissler, Olds & Lowe, P.C.

(57) ABSTRACT

A method for computing an exact solution for an electronic state of a substance by performing a first principle calculation using a computer, the method is characterized in that evaluating a deviation of an approximate value obtained by local density approximation or generalized gradient approximation from the exact solution of the electronic state to be obtained using an energy functional determined by an electronic density, a space derivative for the electronic density and fluctuations of physical quantities; and computing the exact solution by solving an optimization problem being defined by the energy functional.

9 Claims, 3 Drawing Sheets

(51) Int. Cl.
*G06G 7/48* (2006.01)
*G06G 7/56* (2006.01)
*G06F 19/00* (2011.01)
*G06F 17/50* (2006.01)
*G06F 19/16* (2011.01)
*G06F 17/13* (2006.01)

(56) References Cited

U.S. PATENT DOCUMENTS

| 2008/0034287 | A1 | 2/2008 | Mills | |
|---|---|---|---|---|
| 2009/0015447 | A1* | 1/2009 | Kilbank | 341/60 |
| 2009/0093973 | A1 | 4/2009 | Kusakabe | |
| 2009/0177409 | A1* | 7/2009 | Mills | 702/22 |
| 2013/0151174 | A1* | 6/2013 | Kusakabe et al. | 702/57 |

FOREIGN PATENT DOCUMENTS

| JP | 2008-52308 A | 3/2008 |
|---|---|---|
| WO | WO 2007/141942 A1 | 12/2007 |

OTHER PUBLICATIONS

K. Kusakabe, NPL, "A first-principles calculational method for the magnetic impurity problem based on a density-matrix functional theory", 2006.*

Arjan Berger, NPL, "Current-Density Functionals in Extended Systems", 2006.*

Hitoshi Adachi, "Zairyo Kenkyu-yo Daiichi Genri Keisan Program MixedBasis no Shokai", Hitachi to Giho, Dec. 12, 2003, No. 9, pp. 77-83.

Hisazumi Akai, "Daikibo Keisanki Simulation Tokushugo", System/Seigyo/Joho, Jul. 15, 2004, vol. 48, No. 7, pp. 14-18.

Kimiaki Aonuma, Joho System to Tameno Joho Gijutsu Jiten, $1^{st}$ edition, Baifukan Co., Lts., Itaru Yamamoto, 60-30-2006, pp. 3-80, 3-95.

Kasai et al., "Introduction to Computational Materials Design", Oct. 20, 2005.

Mansori Koyama, "Nanosimulation Gijutsu Handbook", $1^{st}$ edition, Kyoritsu Shuppan Co., Ltd., Jul. 15, 2006, pp. 148 to 153, 172 to 173, 190 to 195, 212 to 213, 218, 220 to 231, 370 to 372, 377 to 379, 423 to 425.

Koichi Kusakabe et al., "A Self-consistent First-principles Calculation Scheme for Correlated Electron Systems", Journal of Physics: Condensed Matter, Oct. 18, 2007, IOP Publishing.

Koichi Kusakabe, "Determination of the Mott insulating transition by the multi-reference density functional theory", Journal of Physics: Condensed Matter, Aug. 24, 2007, IOP Publishing.

Koichi Kusakabe, "Multi-reference density funtional theory for Mott's insulators and electron-electron interaction mediated superconductivity", ISSP International workshop and Symposium on the Foundations and Applications of Density Functional Theory, Aug. 1, 2007 to Aug. 3, 2007.

Koichi Kusakabe, "An N representability problem on a twisted boundary condition for the multi-reference density function theory", The $10^{th}$ Asian Workshop on First-Principles Electronic Structure Calculations, Oct. 29, 2007.

Koichi Kusakabe, "An optimization scheme of the extended Kohn-Sham model determined by the multi-reference density functional theory", Int. Conf. on Quantum Simulators and Design (QSD2008), Jun. 2, 2008.

Koichi Kusakabe et al.; "Topology of the extended Kohn-Sham model space and differentiability of the universal energy functional" published on Aug. 25, 2008, physical society of Japan (JPS).

Atsushih Oshiyama, Suri Model no Kakutoku, Journal of the Society of Instrument and Control Engineers, Oct. 10-12, 2002, vol. 41, No. 12, pp. 875-880.

Kazunori Sato et al., "<Kisohen> Kiso Koza, Oyo Butsuri", vol. 75, No. 11, The Japan Society of Applied Physics, Nov. 10, 2006, pp. 1371 to 1376.

Akira Ueda, "Bunshi Simulation", $1^{st}$ print, Kabushiki Kaisha Shokabo, Oct. 25, 2003, pp. 360-373, 403 to 404.

Yeeboon Yun, "Keisan Chino o Mochiita Chikuji Kinji Tamokuteki Saitekika Shuho", Transactions of the Society of Instrument and Control Engineers, vol. 43, No. 8, pp. 672-678.

Berrah S. et al: "The first principle calculation of electronic and optical properties of A1N, GaN and 1nN compounds under hydrostatic pressure", Semiconductor Physics, Quantum Electronics & Optoelectronics, UK, vol. 9, No. 2, Jan. 1, 2006, pp. 12-16, XP007920081.

Faraoun H. I. et al: "Crystalline, electronic, and magnetic structures of [theta]-Fe3C, [chi]-Fe5C2, and [eta]-Fe2C from first principle calculation", Journal of Applied Physics, American Institute of Physics. New York, US, vol. 99, No. 9, May 12, 2006, pp. 93508-093508, XP012084986, ISSN: 0021-8979, DOI: 10.1063/1.2194118.

* cited by examiner

ELECTRONIC STATE COMPUTING METHOD, ELECTRONIC STATE COMPUTING DEVICE, AND RECORDING MEDIUM

CROSS-REFERENCE TO RELATED APPLICATIONS

This application is the national phase under 35 U.S.C. §371 of PCT International Application No. PCT/JP2009/004219 which has an International filing date of Aug. 28, 2009 and designated the United States of America.

FIELD

The present application relates to an electronic state computing method, an electronic state computing device and a recording medium recorded a computer program capable of computing an electronic state of a material by performing a first-principle calculation.

BACKGROUND

Conventionally, there is a calculation theory called a first-principle calculation theory of estimating physical or chemical properties (hereinafter called properties) of a material according to a basic principle of quantum mechanics. As this kind of calculation theory, there is a calculation theory based on a density functional theory, in which properties, such as mechanical properties including elasticity, conductive properties including superconductive properties, a dielectric property and a magnetic property, are reproduced with relatively high accuracy, and a computation scale is in an implementable range. This calculation theory is already applied to material design, and there are numerous examples with its estimation accuracy verified through experiments (for example, see "Keisanki Material Design Nyumon (Introduction to computational material design)" edited by Hideaki Kasai, Hisazumi Akai, Hiroshi Yoshida, Osaka University Press (2005)).

As computation techniques based on a density functional method, a plurality of techniques are known, such as generalized gradient approximation (GGA), GW approximation, GW+Γ approximation and LDA+U approximation, regarded as techniques for solving problems caused by local density approximation (LDA).

However, each of the above-mentioned computation techniques has a problem of not giving a method for reaching a real solution (exact solution). In other words, until now, there is not a self-consistent calculation theory of reaching a real solution while a single-electron basis set being given by LDA in high accuracy is utilized.

On the other hand, the present inventor has proposed a fluctuation reference determination method as an effective many-electron calculation based on a multi-configuration reference density functional method (for example, see WO 2007/141942). With this method, an extended Kohn-Sham equation for reproducing a fluctuation variable (correlation function) having a positive definite property, such as local density fluctuations, in addition to one-electron density is given, whereby the reproduction accuracy of physical quantities can be raised to arbitrary accuracy. With this computation technique, total energy, one-electron density and a specific fluctuation variable of a material are reproduced simultaneously through the determination of the lowest energy state of a model Hamiltonian. Furthermore, by using a model system and its stable solution as initial values, a time-development equation for reproducing total energy, one-electron density and canonical correlation function is given, and a highly-accurate first principle electronic state computing method for reproducing the external field responses (responses to dynamic deformation and electromagnetic field application) of a material is given.

However, the effective many-electron computation based on the aforementioned multi-configuration reference density functional method is a computation technique that inevitably requires reference calculation, such as a Quantum Monte Carlo Method, a Transcorrelated Method, a Configuration Interaction Method, a Perturbation calculation/Green's function Method or an Effective Potential Method. For this reason, the reproduction accuracy of physical quantities depends on the calculation accuracy of the reference calculation, and a calculation technique reaching a real solution beyond the calculation accuracy of the reference calculation is not given.

SUMMARY

The present application was made in view of the above-described circumstances, and an object of the present is to provide an electronic state computing method, an electronic state computing device, and a recording medium capable of obtaining a stable numerical solution in a range permitted by computing resources by starting from a model based on local density approximation or generalized gradient approximation usually used for a density functional method and by giving an approximation model sequence reaching a real solution.

Another object of the present application is to provide an electronic state computing method, an electronic state computing device, and a recording medium capable of giving a procedure approaching an exact solution by determining an optimized model, which is obtained when a space of operators determining fluctuations is extended sequentially, from the estimated value of a directional derivative on the model space of an energy functional without evaluating the energy functional itself.

Still another object of the present application is to provide an electronic state computing method, an electronic state computing device, and a recording medium capable of finding out, as a Cauchy sequence, a numerical sequence formed of groups, wherein each group being comprised of a model Hamiltonian determined when an energy functional is introduced and an order parameter determining an electronic state by obtaining approximate values of functional derivatives in the course of solving an optimization problem.

Yet still another object of the present application is to provide an electronic state computing method capable of guaranteeing the stability of the computed exact solution by obtaining the accumulation point of approximate values in a Banach space of the models.

An electronic state computing method according to the present application is a method for computing an exact solution for an electronic state of a material by performing a first principle calculation using a computer, the method characterized in that a deviation from the exact solution of the electronic state to be obtained to an approximate value obtained by local density approximation or generalized gradient approximation is evaluated using an energy functional determined by a density serving as an order parameter deciding the electronic state, space derivatives of the density and fluctuations of physical quantities; and the exact solution is computed, in a space being composed of a set including a plurality of groups as elements, each group being comprised of a model. Hamiltonian decided when the energy functional is introduced and the order parameter deciding the electronic state, by computing a distance between the elements using the order parameter with respect to the elements included in the set, computing the approximate value regarding a functional derivative of the energy functional; and estimating an asymptotic direction toward the exact solution from approximate values of functional derivatives of the energy functional, on the occasion of solving an optimization problem being defined by the energy functional.

The electronic state computing method according to the present application is characterized in that the space is a Banach space in which the accumulation point of the elements is included in the space and the space includes the exact solution.

An electronic state computing device according to the present application is a device for computing an exact solution for an electronic state of a material by performing a first principle calculation, the device characterized by comprising; means for evaluating a deviation from the exact solution of the electronic state to be obtained to an approximate value obtained by local density approximation or generalized gradient approximation using an energy functional determined by a density serving as an order parameter deciding the electronic state, space derivatives of the density and fluctuations of physical quantities; and the exact solution in a space being composed of a set including a plurality of groups as elements, each group being comprised of a model Hamiltonian decided when the energy functional is introduced and the order parameter deciding the electronic state, by computing a distance between the elements using the order parameter with respect to the elements included in the set, computing the approximate value regarding a functional derivative of the energy functional; and estimating an asymptotic direction toward the exact solution from approximate values of functional derivatives of the energy functional, on the occasion of solving an optimization problem being defined by the energy functional.

A recording medium according to the present application is a recording medium recording a computer program for causing a computer to compute an exact solution for an electronic state of a material by performing a first principle calculation, the computer program is characterized by causing the computer to evaluate a deviation from the exact solution of the electronic state to be obtained to an approximate value obtained by local density approximation or generalized gradient approximation using an energy functional determined by a density serving as an order parameter deciding the electronic state, space derivatives of the density and fluctuations of physical quantities; and causing the computer to compute the exact solution in a space being composed of a set including a plurality of groups as elements, each group being comprised of a model Hamiltonian decided when the energy functional is introduced and the order parameter deciding the electronic state, by computing a distance between the elements using the order parameter with respect to the elements included in the set, computing the approximate value regarding a functional derivative of the energy functional; and estimating an asymptotic direction toward the exact solution from approximate values of functional derivatives of the energy functional, on the occasion of solving an optimization problem being defined by the energy functional.

In the present application, the deviation from an exact solution to an approximate value, inevitably generated by introducing local density approximation or generalized gradient approximation, is evaluated, and the exact solution for an electronic state is obtained in the course of solving an optimization problem being set using an energy functional. Hence, it is possible to give a computation procedure reaching the exact solution by using a model based on the local density approximation or the generalized gradient approximation generally used in a density functional method, as a start point.

The energy functional being used when the approximate value given by the local density approximation or the generalized gradient approximation is obtained may be replaced with an energy functional determined by an analytic function decided by density and space derivatives of the density. Alternatively, the energy functional can also be replaced with an energy functional determined by numerically processing density and space derivatives of the density by a finite number of times.

Furthermore in the present application, the group of a model Hamiltonian and an order parameter deciding an electronic state is regarded as a point on a space, and an asymptotic direction toward the exact solution on the space is estimated from an approximate value of the functional derivative of the energy functional, whereby a procedure approaching to the exact solution can be obtained without evaluating a universal energy functional itself.

Furthermore in the present application, an approximate value of the functional derivative is computed with respect to each element of a set in the course of solving the optimization problem. The model space given by the present application can be a Banach space by deciding the distance between densities using an appropriate norm given by an order parameter and by giving topology. Hence, a step of giving a model sequence by extending an operator space deciding fluctuations and then finding out a Cauchy sequence from the model sequence becomes a procedure for reaching the exact solution.

In the present application, the space is a Banach space in which the accumulation point of appropriate values is contained in the same space and the space contains the exact solution, whereby it is certified that finding out the Cauchy sequence from the model sequence is a procedure reaching the exact solution.

According to the present application, it is possible to give a computation procedure reaching the exact solution by using a model based on the local density approximation or the generalized gradient approximation generally used in a density functional method, as a start point. Hence, the accuracy of an estimate value for the electronic state of a material, computed by the conventional approximation computation technique, is improved significantly; as a result, a theoretical material analysis technique serving as the basis of material design can be provided as a practical computation technique given by the density functional method serving as the first principle computation technique based on Schroedinger's equation.

Furthermore in the present application, it is possible to obtain a procedure approaching an exact solution without evaluating the universal energy functional itself. The approximate value reaches the exact solution serving as a numerical solution since the accuracy is improved by the extension of the operator space.

Furthermore in the present application, the model space given by the present invention can serve as a Banach space containing the exact solution; hence, it is possible to reach the exact solution by giving a model sequence by extending an operator space deciding fluctuations and then by finding out a Cauchy sequence from the model sequence.

In the present application, the space is a Banach space in which the accumulation point of appropriate values is contained in the same space and which contains the exact solution, whereby the exact solution is reached by finding out the Cauchy sequence from the model sequence.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

The present invention will be described below on the basis of the drawings showing its embodiments.

Embodiment 1

A computation principle in an electronic state computing method according to this embodiment will be described below. In this embodiment, its purpose is to numerically obtain, as the exact solution of an electronic state, an order parameter serving as electron density generated when a Coulomb many-body system is generated in a ground state. The energy $E_0$ of the ground state in the Coulomb many-body system is represented by the following expression.

(Mathematical formula 1)
$$E_0 = \min_{X_i}\{\min_{\Psi} G_{LDA+X_i}[\Psi] + \Delta E_{rxc}[n_{LDA+X_i}]\}$$

Here, $G_{LDA+X_i}[\Psi]$ is an energy functional regarding the wave function $\Psi$ of an electron obtained by introducing local density approximation (LDA) and an operator represented by a correlation function representing fluctuations into a first principle calculation as described later. The electron density given by a wave function $\Psi_{LDA+X_i}$ for minimizing $G_{LDA+X_i}[\Psi]$ is $n_{LDA+X_i}$. $\Delta E_{rxc}$ is a residual exchange-correlation energy functional indicating a deviation from the energy $E_0$ of the ground state due to the introduction of the local density approximation, and the electron density given by the wave function $\Psi_{LDA+X_i}$ is used as a variable. $X_i$ is a point defined as $X_i = (H_{LDA+X_i}, n_{LDA+X_i})$ by the group of a model Hamiltonian $H_{LDA+X_i}$ and order parameter $n_{LDA+X_i}$ obtained at the time of local density approximation. Since a point can be obtained each time an operator representing fluctuations is determined, a plurality of points are present. Hence, a set of these points is present. Since the distance between the order parameters $n_{LDA+X_i}$ of different points can be defined, a space can be formed by introducing a phase into this set.

Mathematical formula 1 represents an expression for evaluating the deviation from the exact solution obtained when the local density approximation is introduced into the first principle calculation using the energy functional $G_{LDA+X_i}[\Psi]$ and the residual exchange-correlation energy functional $\Delta E_{rxc}$.

Figure 1:
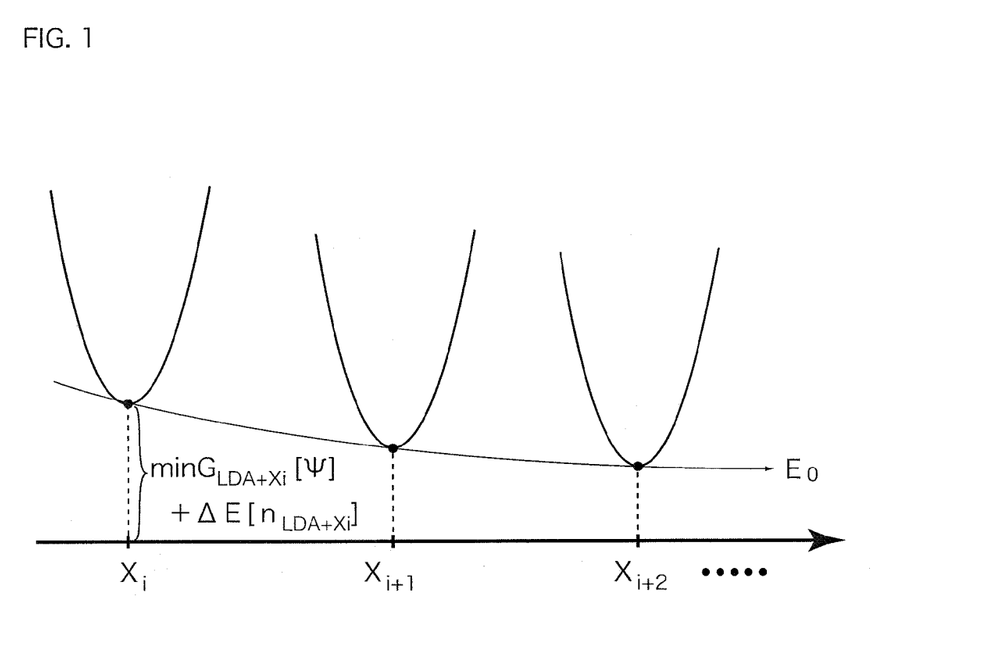
FIG. 1 is a view illustrating a computation principle.

FIG. 1 is an explanatory view illustrating a computation principle. The expression of Mathematical formula 1 represents that the energy $E_0$ of the ground state is obtained by first fixing $X_i$ and minimizing the energy functional $G_{LDA+X_i}[\Psi]$ and by minimizing the sum of the minimized energy functional $G_{LDA+X_i}[\Psi]$ and the residual exchange-correlation energy functional $\Delta E_{rxc}$ determined by $n_{LDA+X_i}$ given by the wave function $\Psi_{LDA+X_i}$ for giving this minimum value inside a space formed by the set constituted by $X_i$. Since the residual exchange-correlation energy functional $\Delta E_{rxc}$ is generally indifferentiable, it is impossible to obtain a minimum value; however, as described later, it is possible to determine an appropriate space (in other words, a space constituted by $X_i$) and to obtain the functional derivative and its approximate value regarding the direction given by continuous parameter change inside the determined space. When the approximate solution given by computation approaches the sufficient neighborhood of a real solution (exact solution) by incorporating the contribution of necessary and sufficient fluctuations into $G_{LDA+X_i}[\Psi]$, the approximate value of the functional derivative asymptotically approaches an exact derivative value. Hence, it is possible to find out the direction asymptotically approaching the exact solution by examining the change in the approximate value of the functional derivative with respect to a point sequence formed when the parameter is changed, for example, $X_i, X_{i+1}, X_{i+2}, \ldots$. In this embodiment, the electron density in the ground state, serving as the exact solution, is obtained as electron density at the time when the minimization in all the directions in which $X_i$ is changed is completed.

In the local density approximation serving as a conventional approximation theory, a self-consistent calculation theory for approaching the real solution while utilizing one electron ground being high in accuracy is not given; hence, it is impossible to perform computation in an electron system in which a strong correlation effect due to the generation of fluctuations in an orbital is generated.

On the other hand, as described later in detail, the expression represented by Mathematical formula 1 is used to obtain the exact solution by evaluating the residual exchange-correlation energy being inevitable in the practical calculation of the first principle calculation, by optimizing (minimizing) the division generated at the time of approximation as the optimization problem of the energy functional and by zeroing the deviation in the end. In other words, Mathematical formula 1 gives a method capable of reaching the exact solution in the range of the accuracy limit of a numerical solution method.

The energy functional $G_{LDA+X_i}[\Psi]$ is defined by the following formula.

(Mathematical formula 2)
$$G_{LDA+X_i}[\Psi] = \langle \Psi | \hat{T} + \hat{V}_{red}^{X_i} | \Psi \rangle + \frac{e^2}{2}\int dr dr' \frac{n_\Psi(r) n_\Psi(r')}{|r-r'|} + E^{LDA}[n_\Psi] + E^{non-local}[n_\Psi] + \int dr n_\Psi(r) v_{ext}(r)$$

Here, $\Psi$ is a many-particle wave function, T is an operator regarding kinetic energy, $V_{red}^{X_i}$ is an operator represented by the correlation function of the following Mathematical formula 3 in which a parameter $X_i^{(n)}$ serving as a continuous variable is introduced. Although the operator T and V in the operator $V_{red}^{X_i}$ are each denoted by a letter with a hat in the mathematical formula, they are denoted without the hat in the specification. Furthermore, e represents the electric charge of an electron, $n_\Psi(r)$ represents the electron density at a position vector r, and $V_{ext}(r)$ represents an external scalar potential.

(Mathematical formula 3)

$$\hat{V}_{red}^{Xi} = \Sigma X_i^{(n)} \left\{ \begin{array}{l} (\hat{Y}_i^{(n)} - \langle \hat{Y}_i^{(n)} \rangle)^\dagger (\hat{Y}_i^{(n)} - \langle \hat{Y}_i^{(n)} \rangle) - \\ (\hat{Z}_i^{(n)} - \langle \hat{Z}_i^{(n)} \rangle)^\dagger (\hat{Z}_i^{(n)} - \langle \hat{Z}_i^{(n)} \rangle) \end{array} \right\}$$

$$\hat{Y}_i^{(n)} = \sum_{l_1, l_2, \sigma} f^{(n)}(l_1, l_2, \sigma) d_{l_1 \sigma}^\dagger d_{l_2 \sigma}$$

$$\hat{Z}_i^{(n)} = \sum_{l_1, l_2, \sigma} \bar{f}^{(n)}(l_1, l_2, \sigma) d_{l_1 \sigma}^\dagger d_{l_2 \sigma}$$

Here, $X_i$ is a point defined as $X_i = (H_{LDA+Xi}, n_{LDA+Xi})$ by the group of a model Hamiltonian $H_{LDA+Xi}$ and the order parameter $n_{LDA+Xi}$ obtained at the time of the local density approximation. The parameter $X_i^{(n)}$ is a non-negative real number and has a property of not diverging infinitely. Furthermore, in the case that indexes $I_1$ and $I_2$ indicating an energy band and a wave number vector and a spin state σ are designated, f and f bar are complex number coefficients determined while being related to each other and are determined using the solution of a Kohn-Sham equation determined in the middle of computation under the limitation regarding a scattering process given at the time of input. Operators $d^+_{l_1\sigma}$ and $d_{l_2\sigma}$ are generation/annihilation operators determined by an orbital given by the solution of the Kohn-Sham equation in which the local density approximation is adopted.

Moreover, $E^{LDA}[n_\Psi]$ and $E^{non-local}[n_\Psi]$ in Mathematical formula 2 are defined as described below and represent computable density functionals.

(Mathematical formula 4)

$$E_{LDA}[n_\Psi] = \int \varepsilon(n_\Psi(r)) n_\Psi(r) dr$$

$$E^{non-local}[n_\Psi] = \sum_{l_1, l_2, \sigma} g(l_1, l_2, \sigma) \langle \Psi | d_{l_1 \sigma}^\dagger d_{l_2 \sigma} | \Psi \rangle$$

Here, $\in(n)$ is a bounded monotonically decreasing continuous function, $g(I_1, I_2, \sigma)$ is a real value coefficient, and these are given at the time of input. Although optimization can be done once again using the solution of the Kohn-Sham equation determined in the middle of the computation process, the definitions do not affect the results, provided that the fluctuations incorporated by the fact that a sufficient computation scale was able to be securely obtained are sufficient.

On the other hand, the residual exchange-correlation energy functional $\Delta E_{rxc}$ is given by the following formula. This expression is appropriate at the initial stage of the computation, and the origin of the λ integration contained in the first and second items on the right side is a point given by a kinetic energy functional.

(Mathematical formula 5)

$$\Delta E_{rxc}[n] = \frac{e^2}{2} \int d\lambda \int dr dr' \frac{1}{|r-r'|} \langle \Psi_n^\lambda | (\hat{n}(r) - n(r))(\hat{n}(r') - n(r')) | \Psi_n^\lambda \rangle -$$

$$\frac{e^2}{2} \int d\lambda \int dr dr' \frac{1}{|r-r'|} \langle \Psi_n^\lambda | \sum_\sigma \Psi_\sigma^\dagger(r) \Psi_\sigma(r) | \Psi_n^\lambda \rangle - E^{LDA}[n] -$$

$$E^{non-local}[n] + \min_{\Psi \to n} \langle \Psi | \hat{T} | \Psi \rangle - \min_{\Psi \to n} \langle \Psi | \hat{T} + \hat{V}_{red}^{LDA+Xi} | \Psi \rangle$$

The present inventor gave a fluctuation reference determination method as effective many-body electron calculation based on a multi-configuration reference density functional method in the specification of PCT/JP 2007/054057. With this determination method, an extended Kohn-Sham equation reproducing a variable (correlation function) having a positive definite property, such as local density fluctuations, in addition to one-electron density is defined (refer to Mathematical formula 6), whereby a practical computing method capable of raising the reproduction accuracy of physical quantities to arbitrary accuracy is obtained.

(Mathematical formula 6)

$$G_{Wi}[\Psi] =$$

$$\langle \Psi | T + V_{red} | \Psi \rangle + \frac{e^2}{2} \int dr dr' \frac{n_\Psi(r) n_\Psi(r')}{|r-r'|} + E_{rxc}[n_\Psi] + \int dr v_{ext}(r) n_\Psi(r)$$

With a model in which the local density approximation is applied to the residual exchange-correlation energy functional in the extended Kohn-Sham equation, it is possible to generate a plurality of models by changing the definition of the fluctuation item. In the group (set) formed by generated models, the distance between the models can be measured by determining an appropriate measure using electron density serving as an order parameter. In other words, the distance $|X_i - X_j|$ between two points can be measured in a space Q formed by the set of points $X_i = (H_{LDA+Xi}, n_{LDA+Xi}(r))$. In addition, in the case that a model sequence converging with respect to a relative distance is made, the space Q becomes a Banach space having a property that the accumulation point thereof is contained in the space Q. It is certified that the space Q contains a point representing the exact solution.

For this reason, a procedure for reaching the real solution is obtained by giving an approximation model sequence by extending an operator space for determining fluctuations to be incorporated and by finding out a Cauchy sequence from the sequence.

Hence, Mathematical formula 1 is defined as a minimization problem on the Banach space (space Q), and the solution of the defined minimization problem is given as the convergence point of the point sequence $\{X_j\}$. Actually, the Gateaux derivative of the residual exchange-correlation energy functional $\Delta E_{rxc}$ on the space Q is defined in the extension direction of the linear operator formed by the continuous change of the parameter $X_i^{(n)}$ with respect to one item contained in the operator $V_{red}^{Xi}$ having the format of Mathematical formula 3, and a one-dimensional search problem is given. This extension direction may be given by concurrently changing the group of the parameters $X_i^{(n)}$ at the same extension ratio.

The asymptotic direction toward the real solution on the above-mentioned model space can be estimated from an approximate value of the functional derivative of the universal energy functional incorporated in the two λ integrations of the residual exchange-correlation energy functional $\Delta E_{rxc}$; as a result, a Cauchy sequence can be generated. Since the accuracy of the approximate value is improved as the operator space is extended, the approximate value can reach the real solution serving as a numerical solution.

The practical numerical solution method of the minimization problem defined as described above will be described specifically. The sixth item on the right side in Mathematical formula 5 is obtained at the time when the minimization of $G_{LDA+Xi}$ is attained. Similarly, in the fifth item, it is possible to obtain a numerical exact solution by solving a potential search problem. Alternatively, with a model subjected to local density approximation, it is also possible to give an approximate value using a one-shot calculation serving as a method for obtaining only the solution of a one-body wave function determined by the extended Kohn-Sham equation while the density is fixed without performing self-consistent calculation. Hence, when the search on the space Q proceeds, a method for approximately obtaining the Gateaux derivative of the two λ integrations contained in the residual exchange-correlation energy functional $\lambda E_{rxc}$ can be given using the model and its wave function obtained when the search proceeds in one direction in which $X_i$ is changed. As a result, it is possible to perform the numerical search of electron density for giving the energy $E_0$ of the ground state without evaluating the residual exchange-correlation energy functional $\Delta E_{rxc}$.

One method for approximately obtaining the Gateaux derivative of the two λ integrations contained in the residual exchange-correlation energy functional $\Delta E_{rxc}$ uses Mathematical formula 7 as described below. Here, $\delta_{xi} E[n]$ is the Gateaux derivative in one direction in which the group of the parameters $X_i^{(n)}$ is infinitesimally changed formally. When the search proceeds sufficiently, in the expression of Mathematical formula 7, the origin of the λ integration of the first item of Mathematical formula 5 is redefined as the sixth item of Mathematical formula 5 already obtained, and the fourth item of Mathematical formula 5 is changed to the self-interaction energy determined by Ψ in Mathematical formula 1 already obtained, and the origin of the λ integration of the second item of Mathematical formula 5 is used as the fourth item of Mathematical formula 5. At this time, it is certified that each of the evaluation formulas of the two functional derivatives of Mathematical formula 7 becomes an exact evaluation formula by virtue of a perturbation theory that uses the fact that the wave function represented in the integrand of the λ integration is obtained by a limited search regarding density.

(Mathematical formula 7)

$$\delta_{X_i} \frac{e^2}{2} \int d\lambda \int dr dr' \frac{1}{|r-r'|} \langle \Psi_n^\lambda | (\hat{n}(r) - n(r))(\hat{n}(r') - n(r')) | \Psi_n^\lambda \rangle \cong$$

$$\frac{e^2}{2} \int dr dr' \frac{1}{|r-r'|} \left\{ \begin{array}{l} \langle \delta_{X_i} \Psi_n^{X_i} | (\hat{n}(r) - n(r))(\hat{n}(r') - n(r')) | \Psi_n^{X_i} \rangle + \\ \langle \Psi_n^{X_i} | (\hat{n}(r) - n(r))(\hat{n}(r') - n(r')) | \delta_{X_i} \Psi_n^{X_i} \rangle \end{array} \right\}$$

$$\delta_{X_i} \frac{e^2}{2} \int d\lambda \int dr dr' \frac{1}{|r-r'|} \langle \Psi_n^\lambda | \sum_\sigma \psi_\sigma^\dagger(r) \psi_\sigma(r') | \Psi_n^\lambda \rangle \cong \frac{e^2}{2} \int dr dr' \frac{1}{|r-r'|}$$

$$\left\{ \langle \delta_{X_i} \Psi_n^{X_i} | \sum_\sigma \psi_\sigma^\dagger(r) \psi_\sigma(r') | \Psi_n^{X_i} \rangle + \langle \Psi_n^{X_i} | \sum_\sigma \psi_\sigma^\dagger(r) \psi_\sigma(r') | \delta_{X_i} \Psi_n^{X_i} \rangle \right\}$$

In the above-mentioned minimization problem, in the case that the function $E_{rxc}[n]$ on the space Q has a many-valley property and is difficult to be analyzed numerically, a method, such as simulated annealing, meta dynamics, parallel search or genetic algorithm, can be given as the extension of a known numerical analytical method to eliminate numerical instability and to form a path to an optimum solution.

Figure 2:
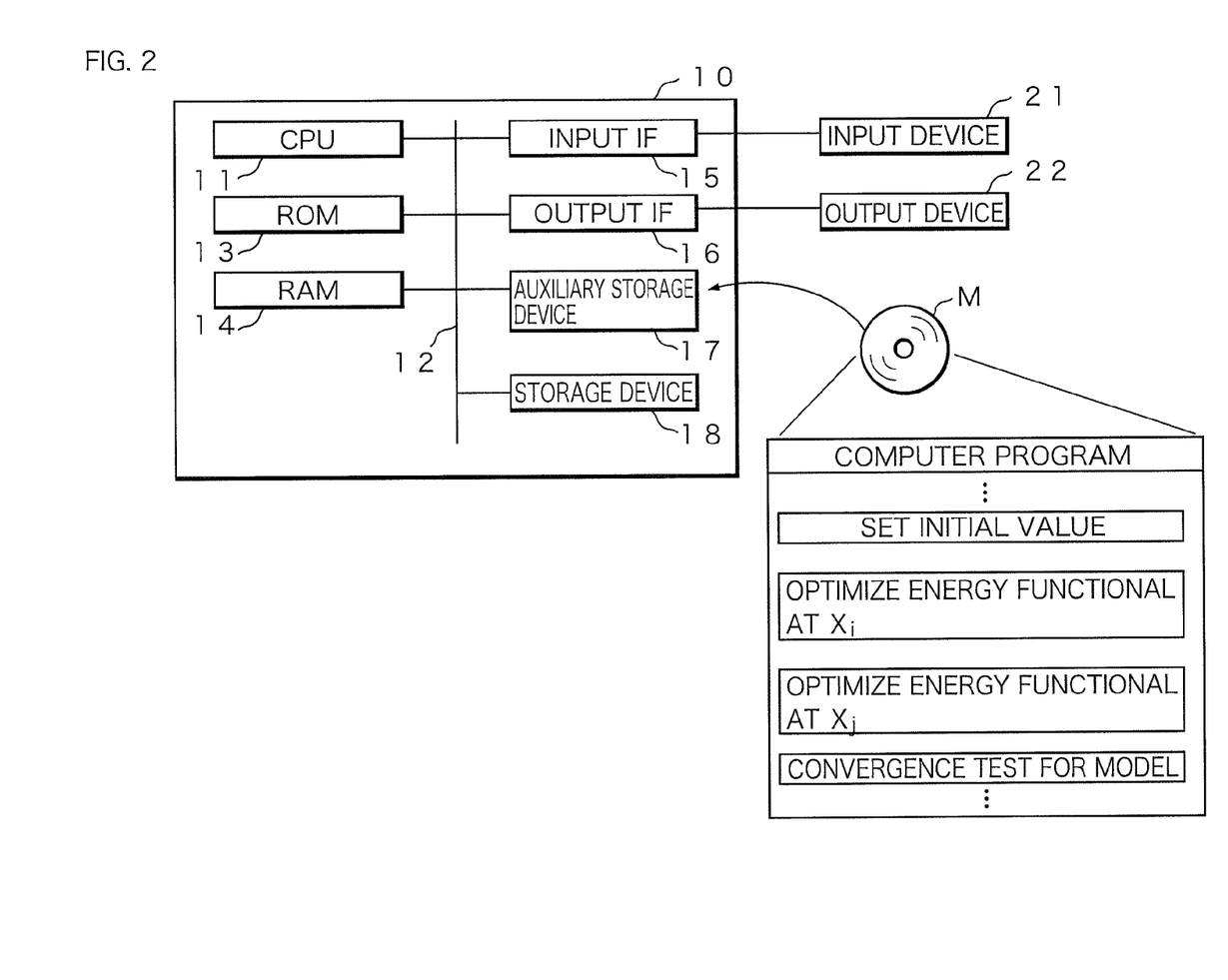
FIG. 2 is a block diagram illustrating an internal structure of an electronic state computing device according to an embodiment.

FIG. 2 is a block diagram illustrating an internal structure of an electronic state computing device according to this embodiment. The electronic state computing device 10 is equipped with a CPU 11, a ROM 13, a RAM 14, an input IF 15, an output IF 16, an auxiliary storage device 17 and a storage device 18, and each hardware of these is connected to one another via a bus 12. A control program for controlling each part of the hardware is stored in the ROM 13. The CPU 11 controls each part of the aforementioned hardware by loading and executing the control program stored in the ROM 13 on the RAM 14. An input device 21, such as a mouse and a keyboard, are connected to the input IF 15. On the other hand, an output device 22, such as a CRT or a liquid crystal display, is connected to the output IF 16.

The auxiliary storage device 17 is equipped with a reading device, such as an FD drive and a CD-ROM drive, for reading the aforementioned computer program from a recording medium M, such as an FD and a CD-ROM, having recorded the computer program for realizing an electronic state computation method described in this embodiment using a computer. The computer program read by the auxiliary storage device 17 is stored in the storage device 18. The CPU 11 serving as a computing means causes the entire device to function as the electronic state computation device according to the present invention by loading and executing the computer program stored in the storage device 18 on the RAM 14 serving as a storing means. In the RAM 14, various kinds of information being input through the input device 21, the intermediate results and the final results of computations executed by the CPU 11, etc. in addition to the above-mentioned computer program are stored.

As the recording medium M for recording the computer program, other than the aforementioned FD and CD-ROM, it is also possible to utilize an optical disc, such as an MO, an MD or a DVD-ROM; a magnetic recording medium, such as a hard disk; a card type recording medium, such as an IC card, a memory card or an optical card; and a semiconductor memory, such as a mask ROM, an EPROM (Erasable Programmable Read Only Memory), an EEPROM (Electrically Erasable Programmable Read Only Memory) or a flash ROM. In addition, by constituting a system in which a communication network, such as the Internet, can be connected, the aforementioned computer program may be downloaded from the communication network. Furthermore, the aforementioned computer program may also be stored in the ROM 13 in advance.

In the computer program recorded on the recording medium M, an evaluation formula using the aforementioned energy functional $G_{LDA+Xi}[\Psi]$ and residual exchange-correlation energy functional $\Delta E_{rxc}$ and a computing program for optimizing this evaluation formula are contained.

The storage device 18 is, for example, a hard disk drive, in which the computer program read by the auxiliary storage device 17, initial data necessary for computing an electronic state and final results obtained by the computation of the electronic state are stored. Furthermore, a part of the storage area of the storage device 18 is utilized as a computing program storage area in which computing programs based on existing computation techniques, such as a Quantum Monte Carlo Method, a numerical renormalization group method, a dynamic mean field approximation method and an MD calculation method (MD: molecular dynamics) described later.

When the electronic state is computed, the computer program, the initial data, etc. stored in the storage device 18 are read and stored temporarily in the RAM 13. The CPU 11 of the electronic state computing device 10 executes the computer program stored in the RAM 13, thereby computing the electronic state.

Figure 3:
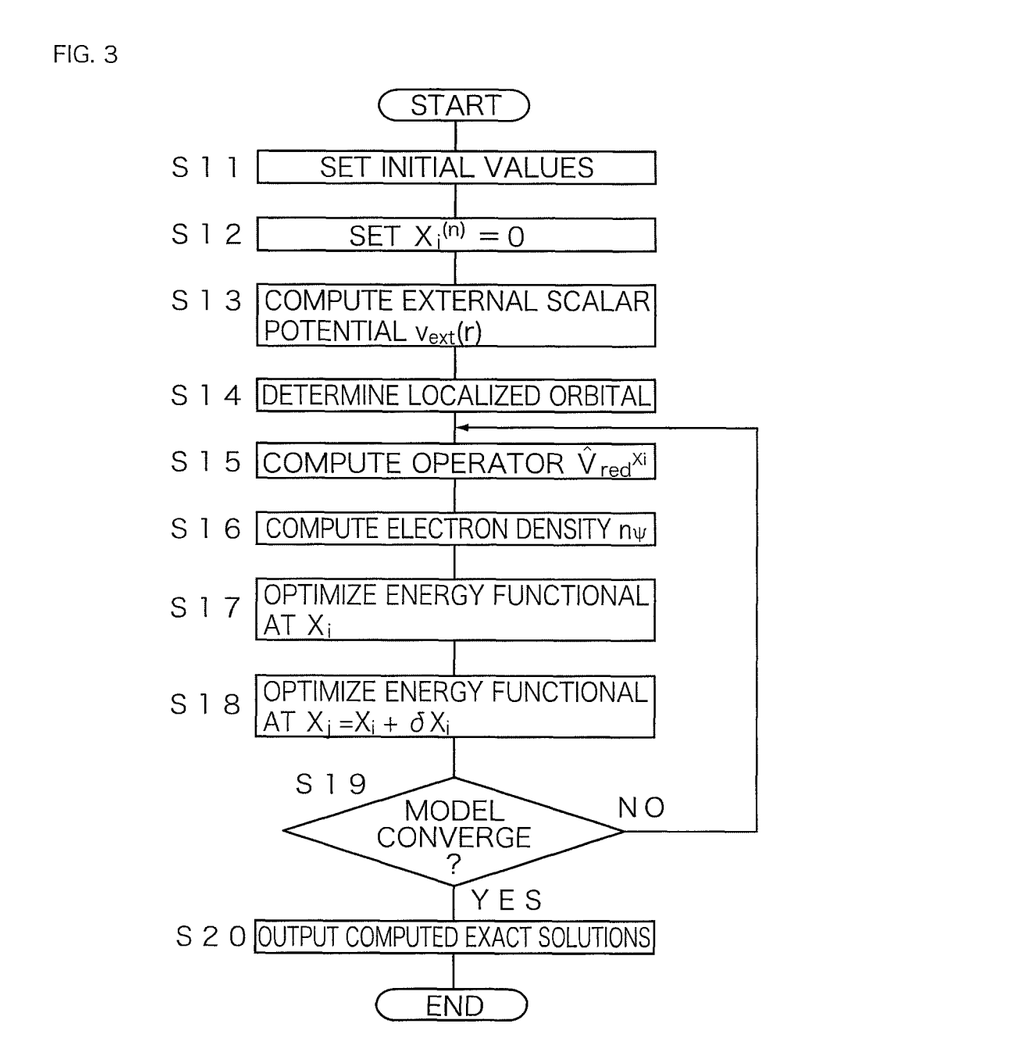
FIG. 3 is a flowchart showing a procedure of processing executed by the electronic state computing device.

A computation procedure for determining the optimum solution of the electronic state will be described below. In this embodiment, a procedure for obtaining the electron density in the ground state using optimization calculation to determine the electronic state for a known crystal structure will be described. FIG. 3 is a flowchart showing a procedure of processing executed by the electronic state computing device 10.

First, the electronic state computing device 10 sets initial values (at step S11). As the setting of the initial values, the crystal structure of a material to be computing and the atomic numbers of atoms constituting the crystal structure are received through the input device 21, and the information of the crystal structure and the atomic numbers are stored in the RAM 14 through the input IF 15. Furthermore, parameters and functions required in computation processes are received through the input device 21, and the parameters and functions incorporated into the device through the input IF 15 are stored. The parameters and functions to be set as the initial values include the complex number coefficients f and f bar of Mathematical formula 3, and the bounded monotonically decreasing continuous function $\in(r)$ and the real value coefficient $g(I_1, I_2, \sigma)$ of Mathematical formula 4.

This embodiment is configured to set the initial values by storing the parameters, etc. received through the input device 21 in the RAM 14; however, the embodiment may also be configured to set the initial values by storing these parameters, etc. in the storage device 18 in advance, by causing the CPU 11 to read the parameters, etc. from the storage device 18 at step S11 and by storing the read parameters, etc. in the RAM 14.

Next, the electronic state computing device 10 sets the parameters $X_i^{(n)}$ of all the elements of the point sequence $\{X_i\}$ to zero (at step S12). More specifically, the CPU 11 secures a storage area for storing the various elements of the point sequence $\{X_i\}$ in the RAM 14 and stores zero as the values of the parameters of the elements in the secured storage area.

In the case that the parameters of all the elements of the point sequence $\{X_i\}$ are set to zero, the expression of Mathematical formula 2 gives genuine local density approximation and can be represented by the following energy functional.

(Mathematical formula 8)

$$G_{LDA}[\Psi] = \langle \Psi|\hat{T}|\Psi\rangle + \frac{e^2}{2}\int dr dr' \frac{n_\Psi(r)n_\Psi(r')}{|r-r'|} +$$

$$E^{LDA}[n_\Psi] + E^{non\text{-}local}[n_\Psi] + \int dr n_\Psi(r) v_{ext}(r)$$

Next, the CPU 11 of the electronic state computing device 10 computes an external scalar potential $V_{ext}(r)$ using the set initial values (at step S13). The external scalar potential $V_{ext}(r)$ can be computed using an ordinary Kohn-Sham equation.

Then, the CPU 11 of the electronic state computing device 10 numerically solves the extended Kohn-Sham equation and computes a localized orbital (at step S14). When based on a density functional method, it is possible to define the effective potential that is given as a density variation of the energy functional including the exchange energy and the correlation energy. In other words, it is possible to obtain the expression that a virtual electron system is moved in the effective single-body Hamiltonian composed of a kinetic energy portion and an effective potential of the Hamiltonian. In this case, the expression of a localized orbital can be obtained, as a solution of the effective single-body Hamiltonian, from a Wannier function immediately obtained by inverse Fourier transformation generalized from a group of appropriate band indices after a Bloch wave was obtained, when, for example, crystallization is taken into consideration. Generally, as such a localized orbital, there generate a group of orbitals in which the number of occupancy is allowed to fluctuate in a quantized energy structure that appears in the effective single-body Hamiltonian. A number operator $n_i$ for evaluating the fluctuations can be defined in association with a group $\phi_i$ of an orthonormalized localized orbital for expressing a level in the vicinity of the Fermi level. Moreover, the creation/annihilation operators $d^+_{11o}$ and $d_{12o}$ can be defined in association with the normalized orbital $\phi_i(r)$.

The CPU 11 of the electronic state computing device 10 determines the notation of a Y operator and a Z operator as shown in Mathematical formula 3 by the redetermination of the complex number coefficients f and f bar that can be defined in association with $\phi_i$ using the expression of the obtained localized orbital, and determines the operator $V_{red}^{Xi}$ with respect to the point $X_i$ (at step S15). Furthermore, since the aforementioned number operator $n_i$ is an operator for measuring the number of electrons on the localized orbital, the CPU 11 obtains a quantum state $|\Psi\rangle$ using the operator $V_{red}^{Xi}$ determined at step S15, obtains $\langle\Psi|n_i|\Psi\rangle$ as an expected value of the number operator $n_i$, and obtains $\langle\Psi|d^+_{11o}d_{12o}|\Psi\rangle$ as the expected value of the operator $d^+_{11o}d_{12o}$, thereby computing electron density $n_\Psi$ (at step S16).

Next, the CPU 11 of the electronic state computing device 10 performs self-consistent calculation in which the processing from step S14 to step S16 is repeated using the electron density $n_\Psi$ computed at step S16, thereby performing optimization (minimization) at the point $X_i$ of the energy functional $G_{LDA+Xi}$ shown in Mathematical formula 1 (at step S17). The optimum value (minimum value) at the computed point $X_i$ is stored in the RAM 14.

Then, the element (that is, point $P_j(j\neq 1)$) contained in the point sequence $\{X_i\}$ is set by minimally changing its parameter $X_j^{(n)}$ from $X_i^{(n)}$ numerically by $\delta X_i^{(n)}$, and self-consistent calculation similar to that described above is performed, whereby optimization (minimization) at each point $X_j$ of the energy functional $G_{LDA+Xi}$ is performed (at step S18). The computed optimum value (minimum value) at each point $X_j$ is stored in the RAM 14.

$\delta X_i$ is described to denote the direction in which the point $X_i$ determined by the group $\{\delta X_i^{(n)}\}$ of the change of the parameter is changed.

As described above, when the search on the space Q formed of the point sequence $\{X_i\}$ proceeds, a method for approximately obtaining the Gateaux derivative of the two $\lambda$ integrations contained in the residual exchange-correlation energy functional $\Delta E_{rxc}$ can be given using the model and its wave function obtained when search proceeds in the $X_i$ direction. In other words, the evaluation of the integrand at $\lambda=0$ is performed by using the solution $\psi_n^{Xi}$ given by $G_{LDA+Xi}$ as a start point, and the change amount of the integration in the direction of $\delta X_i$ on the basis of Mathematical formula 7 is evaluated by redefining integration as described above, whereby it is possible to obtain the derivative of the two $\lambda$ integrations contained in the residual exchange-correlation energy functional $\Delta E_{rxc}$. With only this derivative, the electron density $n_\Psi$ and the quantum state $|\Psi\rangle$ can be made close to real values.

Hence, the CPU 11 of the electronic state computing device 10 examines the change of the energy functional $G_{LDA+Xi}$ when the point is changed inside the space Q in the direction of $\delta X_i$ and judges whether the current model converges (at step S19). In the case that the current model does not converge (NO at step S19), the CPU 11 returns the processing to step S15 and changes the notations of the Y operator and the Z operator, thereby changing the model. At this time, a new model is set by incorporating the combination of bands missing in the previous Y operator and Z operator or by incorporating other bands.

In the case that it is judged that the current model converges at step S19 (YES at step S19), the real values (exact solutions)

can be obtained with respect to the electron density $n_\Psi$ and the quantum state $|\Psi\rangle$. Then, the CPU 11 of the electronic state computing device 10 writes the obtained exact solutions in the storage device 18 and outputs them to the output device 22 as necessary (at step S20).

Since the electron density $n_\Psi$ and the quantum state $|\Psi\rangle$ can be obtained as described above, a bulk order can be determined by determining a coefficient matrix of the effective many-body wave function using an existing computation technique, such as an exact diagonalization method, the Quantum Monte Carlo method, a numerical renormalization group method or a dynamic mean field approximation method.

In this embodiment, a technique in which the local density approximation is applied to the first principle calculation to reach an exact solution has been described; however, it is possible to reach the exact solution in the electronic state using exactly the same procedure by applying appropriate generalized gradient approximation instead of the local density approximation. In the case that the generalized gradient approximation is applied, computation is performed while the first formula of Mathematical formula 4 is replaced with the following Mathematical formula 9.

$$E^{GGA}[n] = \int f(n(r), \nabla n(r)) dr \qquad \text{(Mathematical formula 9)}$$

Here, n(r) represents density, and $\nabla n(r)$ represents a gradient formed by the space derivative coefficients of the density. f represents energy density determined by these function values.

Embodiment 2

With respect to the electronic state computing method according to the present invention, Embodiment 2 is disclosed below.

Since the hardware configuration of the electronic state computing device for implementing the electronic state computing method described in this embodiment is exactly the same as that according to Embodiment 1, its description is omitted.

As in Embodiment 1, the purpose of this embodiment is to numerically obtain, as the exact solution of an electronic state, an order parameter serving as electron density generated when a Coulomb many-body system is generated in a ground state. The energy $E_0$ of the ground state in the Coulomb many-body system is represented by Mathematical formula 1.

Here, the energy functional $G_{LDA+Xi}[\Psi]$ shown in Mathematical formula 1 is defined by the following formula.

(Mathematical formula 10)

$$G_{LDA+X_i}[\Psi] = \langle \Psi | \hat{T} + \hat{V}_{red}^{X_i} | \Psi \rangle + \frac{e^2}{2} \int dr dr' \frac{n_\Psi(r) n_\Psi(r')}{|r-r'|} +$$

$$E^{LDA}[n_\Psi] + E^{non\text{-}local}[\Psi] + \int dr n_\Psi(r) v_{ext}(r)$$

Here, $\Psi$ is a many-particle wave function, T is an operator regarding kinetic energy, $V_{red}^{Xi}$ is an operator represented by the correlation function of the following Mathematical formula 11 in which a parameter $X_i^{(n)}$ serving as an effective interaction parameter is introduced. Although the operator T and V in the operator $V_{red}^{Xi}$ are each denoted by a letter with a hat in the mathematical formula, they are denoted without the hat in the specification. Furthermore, e represents the electric charge of an electron, $n_\Psi(r)$ represents the electron density given by $\Psi$ at a position vector r, and $V_{ext}(r)$ represents an external scalar potential.

(Mathematical formula 11)

$$\langle \Psi | \hat{V}_{red}^{X_i} | \Psi \rangle =$$

$$\sum_n X_i^{(n)} \left[ \begin{array}{c} \sum_{l_1,l_2,l_3,l_4} \sum_{\sigma,\sigma'} \left\{ \begin{array}{c} (f^{(n)}(l_4, l_1, \sigma))^* f^{(n)}(l_2, l_3, \sigma') - \\ (\bar{f}^{(n)}(l_4, l_1, \sigma))^* \bar{f}^{(n)}(l_2, l_3, \sigma') \end{array} \right\} \times \\ \langle \Psi | d_{l_1,\sigma}^\dagger d_{l_2,\sigma'}^\dagger d_{l_3,\sigma'} d_{l_4,\sigma} | \Psi \rangle - \\ (\langle \Psi | \hat{Y}_i^{(n)} | \Psi \rangle)^\dagger \langle \Psi | \hat{Y}_i^{(n)} | \Psi \rangle + (\langle \Psi | \hat{Z}_i^{(n)} | \Psi \rangle)^\dagger \langle \Psi | \hat{Z}_i^{(n)} | \Psi \rangle \end{array} \right]$$

$$\hat{Y}_i^{(n)} = \sum_{l_1,l_2,\sigma} f^{(n)}(l_1, l_2, \sigma) d_{l_1\sigma}^\dagger d_{l_2\sigma}$$

$$\hat{Z}_i^{(n)} = \sum_{l_1,l_2,\sigma} \bar{f}^{(n)}(l_1, l_2, \sigma) d_{l_1\sigma}^\dagger d_{l_2\sigma}$$

Here, $X_i$ is a point defined as $X_i = (H_{LDA+Xi}, n_{LDA+Xi})$ by the group of a model Hamiltonian $H_{LDA+Xi}$ and the order parameter $n_{LDA+Xi}$ obtained at the time of the local density approximation. The parameter $X_i^{(n)}$ is a non-negative real number and has a property of not diverging infinitely. Furthermore, in the case that indexes $I_i$ and $I_2$ indicating an energy band and a wave number vector and a spin state $\sigma$ are designated, f and f bar are complex number coefficients determined while being related to each other and are determined using the solution of a Kohn-Sham equation determined in the middle of computation under the limitation regarding a scattering process given at the time of input. Operators $d^+_{11\sigma}$ and $d_{12\sigma}$ are generation/annihilation operators determined by an orbital given by the solution of the Kohn-Sham equation in which the local density approximation is adopted.

Moreover, $E^{LDA}[n_\Psi]$ and $E^{non\text{-}local}[\Psi]$ in Mathematical formula 10 are defined as described below and represent computable density functionals.

(Mathematical formula 12)

$$E^{LDA}[n_\Psi] = \int \varepsilon(n_\Psi(r)) n_\Psi(r) dr$$

$$E^{non\text{-}local}[\Psi] = \sum_{l_1,l_2,\sigma} g(l_1, l_2, \sigma) \langle \Psi | d_{l_1\sigma}^\dagger d_{l_2\sigma} | \Psi \rangle$$

Here, $\in(n)$ is a bounded monotonically decreasing continuous function, $g(I_1, I_2, \sigma)$ is a real value coefficient, and these are given at the time of input. Although optimization can be done once again using the solution of the Kohn-Sham equation determined in the middle of the computation process, the definitions do not affect the results, provided that the fluctuations incorporated by the fact that a sufficient computation scale was able to be securely obtained are sufficient.

On the other hand, the residual exchange-correlation energy functional $\Delta E_{rxc}$ is given by the following formula. This expression is appropriate at the initial stage of the computation, and the origin of the $\lambda$ integration contained in the first and second items on the right side is a point given by a kinetic energy functional. $\Psi_n^\lambda$ represents a wave function for minimizing the sum of the kinetic energy and the Coulomb interaction increased $\lambda$ times, among those in which the density n(r) is reproduced when the Coulomb interaction is increased λ times. Furthermore, n(r) denoted by n with a hat represents a density operator at a position r. In this expression, $\Psi_\sigma^\dagger(r)$ or $\Psi_\sigma(r)$ is an operator in a field in which an electron having spin σ is generated or annihilated at the position (r).

(Mathematical formula 13)

$$\Delta E_{rxc}[n] = \frac{e^2}{2}\int d\lambda \int drdr' \frac{1}{|r-r'|}\langle\Psi_n^\lambda|(\hat{n}(r)-n(r))(\hat{n}(r')-n(r'))|\Psi_n^\lambda\rangle -$$
$$\frac{e^2}{2}\int d\lambda \int drdr' \frac{1}{|r-r'|}\left\langle\Psi_n^\lambda\left|\sum_\sigma \psi_\sigma^\dagger(r)\psi_\sigma(r')\delta(r-r')\right|\Psi_n^\lambda\right\rangle +$$
$$\min_{\Psi\to n}\langle\Psi|\hat{T}|\Psi\rangle - E^{LDA}[n] - \min_{\Psi\to n}\{\langle\Psi|\hat{T}+\hat{V}_{red}^{Xi}|\Psi\rangle + E^{non-local}[\Psi]\}$$

The present inventor gave a fluctuation reference determination method as effective many-body electron calculation based on a multi-configuration reference density functional method in the specification of PCT/JP 2007/054057. With this determination method, an extended Kohn-Sham equation reproducing a variate (correlation function), such as local density fluctuations, in addition to one-electron density and given by an energy functional having a positive definite property is defined (refer to Mathematical formula 6), whereby a practical computing method capable of raising the reproduction accuracy of physical quantities to arbitrary accuracy is obtained.

With a model in which the local density approximation is applied to the residual exchange-correlation energy functional in the extended Kohn-Sham equation, it is possible to generate a plurality of models by changing the definition of the fluctuation item. In the group (set) formed by generated models, the distance between the models can be measured using electron density serving as an order parameter by determining an appropriate measure. In other words, the distance $|X_i-X_j|$ between two points can be measured in a space Q formed by the set of points $X_i=(H_{LDA+Xi}, n_{LDA+Xi}(r))$. In addition, in the case that a model sequence converging with respect to a relative distance is created, the space Q becomes a Banach space having a property that the accumulation point thereof is contained in the space Q. It is certified that the space Q contains a point representing the exact solution.

For this reason, a procedure for reaching the real solution is obtained by giving an approximation model sequence by extending an operator space for determining fluctuations to be incorporated and by finding out a Cauchy sequence from the sequence.

Hence, Mathematical formula 1 is defined as a minimization problem on the Banach space (space Q), and the solution of the defined minimization problem is given as the convergence point of the point sequence $\{X_j\}$. Actually, the Gateaux derivative of the residual exchange-correlation energy functional $\Delta E_{rxc}$ on the space Q is defined in the extension direction of the linear operator formed by the continuous change of the parameter $X_i^{(n)}$ with respect to one item contained in the operator $V_{red}^{Xi}$ having the format of Mathematical formula 3, and a one-dimensional search problem is given. This extension direction may be given by concurrently changing the group of the parameters $X_i^{(n)}$ at the same extension ratio.

The asymptotic direction toward the real solution on the above-mentioned model space can be estimated from an approximate value of the functional derivative of the universal energy functional incorporated in the two λ integrations of the residual exchange-correlation energy functional $\Delta E_{rxc}$; as a result, a Cauchy sequence can be generated. Since the accuracy of the approximate value is improved as the operator space is extended, the approximate value can reach the real solution as a numerical solution.

The practical numerical solution method of the minimization problem defined as described above will be described specifically. The fifth item and the fourth item on the right side in Mathematical formula 13 are obtained at the time when the minimization of $G_{LDA+Xi}$ is attained. Similarly, in the third item, it is possible to obtain a numerical exact solution by solving a potential search problem. Alternatively, with a model subjected to local density approximation, it is also possible to give an approximate value using a one-shot calculation serving as a method for obtaining only the solution of a one-body wave function determined by the extended Kohn-Sham equation while the density is fixed without performing self-consistent calculation. Furthermore, when the search on the space Q proceeds, a method for approximately obtaining the Gateaux derivative of the two λ integrations contained in the residual exchange-correlation energy functional $\Delta E_{rxc}$ can be given using the model and its wave function obtained when the search proceeds in one direction in which $X_i$ is changed. As a result, it is possible to perform the numerical search of electron density for giving the energy $E_0$ of the ground state without evaluating the residual exchange-correlation energy functional $\Delta E_{rxc}$.

One method for approximately obtaining the Gateaux derivative of the two λ integrations contained in the residual exchange-correlation energy functional $\Delta E_{rxc}$ is described below. Here, $\delta_{xi}E[n]$ is the Gateaux derivative in one direction in which the group of the parameters $X_i^{(n)}$ is infinitesimally changed formally. It is certified that when the search proceeds sufficiently, the expression of Mathematical formula 14 becomes an exact evaluation formula by virtue of an expression that is obtained by expressing the λ integration shown in Mathematical formula 13 using a universal energy functional.

(Mathematical formula 14)

$$\delta_{X_i}\left\{\begin{array}{l}\frac{e^2}{2}\int d\lambda\int drdr'\frac{1}{|r-r'|}\langle\Psi_n^\lambda|(\hat{n}(r)-n(r))(\hat{n}(r')-n(r'))|\Psi_n^\lambda\rangle-\\ \frac{e^2}{2}\int d\lambda\int drdr'\frac{1}{|r-r'|}\left\langle\Psi_n^\lambda\left|\sum_\sigma \psi_\sigma^\dagger(r)\psi_\sigma(r')\delta(r-r')\right|\Psi_n^\lambda\right\rangle\end{array}\right\}\cong$$

$$\frac{e^2}{2}\int drdr'\frac{1}{|r-r'|}\left\{\begin{array}{l}\left\langle\delta_{X_i}\Psi_n^{X_i}\left|\sum_{\sigma,\sigma'}\psi_\sigma^\dagger(r)\psi_{\sigma'}^\dagger(r')\psi_{\sigma'}(r')\psi_\sigma(r)\right|\Psi_n^{X_i}\right\rangle+\\ \left\langle\Psi_n^{X_i}\left|\sum_{\sigma,\sigma'}\psi_\sigma^\dagger(r)\psi_{\sigma'}^\dagger(r')\psi_{\sigma'}(r')\psi_\sigma(r)\right|\delta_{X_i}\Psi_n^{X_i}\right\rangle-\\ 2n(r)(\langle\delta_{X_i}\Psi_n^{X_i}|\hat{n}(r')|\Psi_n^{X_i}\rangle+\langle\Psi_n^{X_i}|\hat{n}(r')|\delta_{X_i}\Psi_n^{X_i}\rangle)\end{array}\right\}-$$

$$(\langle\delta_{X_i}\Psi_n^{X_i}|\hat{T}|\Psi_n^{X_i}\rangle+\langle\Psi_n^{X_i}|\hat{T}|\delta_{X_i}\Psi_n^{X_i}\rangle)$$

A specific computing procedure using the aforementioned computation principle is the same as that according to Embodiment 1, whereby an exact solution is computed using exactly the same computation procedure as that shown in FIG. 3.

Furthermore, in the above-mentioned minimization problem, in the case that the function $E_{rxc}[n]$ on the space Q has a many-valley property and is difficult to be analyzed numerically, a method, such as simulated annealing, meta dynamics, parallel search, genetic algorithm or multi-canonical ensemble, can be given as the extension of a known numerical analytical method to eliminate numerical instability and to form a path to an optimum solution.

In Embodiments 1 and 2, although the optimization calculation of the electronic state for a known crystal structure has been described, the dynamics of the system can also be computed using the technique of molecular dynamics. For the purpose of computing the dynamics of the system, the effective many-body wave function in a certain time development step is obtained, and MD computation (MD: Molecular Dynamics) is performed for a bulk order. In this MD computation, a technique is adopted in which first, an atomic force and a stress are obtained using the electron density, the external scalar potential and the localized orbital obtained by the extended Kohn-Sham theory, the change rate of a material structure is computed on the basis of the obtained atomic force and stress, and the material structure after a micro time is determined sequentially.

The ground state determined according to Embodiment 1 or 2 or the ground state obtained depending on the mode of the molecular dynamics and determined highly accurately can be used continuously as an initial condition for a time-dependent problem. With this method, it is possible to realize a time-dependent current density functional method wherein electron density and current density are used as basic order parameters.

The invention claimed is:

1. A method for computing an exact solution for an electronic state of a crystal structure by performing a first principle calculation using a computer, the method comprising:
evaluating a deviation from the exact solution of the electronic state of the crystal structure to be obtained to an approximate value obtained by local density approximation or generalized gradient approximation using an energy functional determined by a density serving as an order parameter deciding the electronic state, space derivatives of the density and fluctuations of physical quantities; and
computing the exact solution, in a space being composed of a set including a plurality of groups as elements, each group being comprised of a model Hamiltonian decided when the energy functional is introduced and the order parameter deciding the electronic state, by
generating the elements, based on whether a distance between the elements meets a given convergence, comprising
computing a distance between the elements using the order parameter with respect to the elements included in the set,
if the distance between the groups meets the given convergence then generating the exact solution of the electron state of the crystal structure based on the elements and terminating, else
computing the approximate value regarding a functional derivative of the energy functional,
estimating an asymptotic direction toward the exact solution from approximate values of functional derivatives of the energy functional,
incrementing the order parameter of the respective model Hamiltonians of the groups, based at least in part on the estimated asymptotic direction, and
repeating the generating the elements.

2. The electronic state computing method according to claim 1, wherein the space is a Banach space in which the accumulation point of the elements is included in the space and the space includes the exact solution.

3. The method of claim 1 wherein the deviation is a residual exchange-correlation energy functional.

4. A device for computing an exact solution for an electronic state of a crystal structure by performing a first principle calculation comprising:
means for evaluating a deviation from the exact solution of the electronic state of the crystal structure to be obtained to an approximate value obtained by local density approximation or generalized gradient approximation using an energy functional determined by a density serving as an order parameter deciding the electronic state, space derivatives of the density and fluctuations of physical quantities; and
means for computing the exact solution, in a space being composed of a set including a plurality of groups as elements, each group being comprised of a model Hamiltonian decided when the energy functional is introduced and the order parameter deciding the electronic state, by
generating the elements, based on whether a distance between the elements meets a given convergence, comprising
computing a distance between the elements using the order parameter with respect to the elements included in the set,
if the distance between the groups meets the given convergence then generating the exact solution of the electron state of the crystal structure based on the elements and terminating, else
computing the approximate value regarding a functional derivative of the energy functional,
estimating an asymptotic direction toward the exact solution from approximate values of functional derivatives of the energy functional,
incrementing the order parameter of the respective model Hamiltonians of the groups, based at least in part on the estimated asymptotic direction, and
repeating the generating the elements.

5. The device of claim 4 wherein the deviation is a residual exchange-correlation energy functional.

6. A device for computing an exact solution for an electronic state of a crystal structure by performing a first principle calculation comprising a processor performing operations of:
evaluating a deviation from the exact solution of the electronic state of the crystal structure to be obtained to an approximate value obtained by local density approximation or generalized gradient approximation using an energy functional determined by a density serving as an order parameter deciding the electronic state, space derivatives of the density and fluctuations of physical quantities; and
computing the exact solution, in a space being composed of a set including a plurality of groups as elements, each group being comprised of a model Hamiltonian decided when the energy functional is introduced and the order parameter deciding the electronic state, by
generating the elements, based on whether a distance between the elements meets a given convergence, comprising
computing a distance between the elements using the order parameter with respect to the elements included in the set,
if the distance between the groups meets the given convergence then generating the exact solution of the electron state of the crystal structure based on the elements and terminating, else computing the approximate value regarding a functional derivative of the energy functional, estimating an asymptotic direction toward the exact solution from approximate values of functional derivatives of the energy functional, incrementing the order parameter of the respective model Hamiltonians of the groups, based at least in part on the estimated asymptotic direction, and repeating the generating the elements.

7. The device of claim 6 wherein the deviation is a residual exchange-correlation energy functional.

8. A non-transitory computer-readable recording medium recording a computer program for causing a computer to compute an exact solution for an electronic state of a crystal structure by performing a first principle calculation, the computer program comprising:

causing the computer to evaluate a deviation from the exact solution of the electronic state of the crystal structure to be obtained to an approximate value obtained by local density approximation or generalized gradient approximation using an energy functional determined by a density serving as an order parameter deciding the electronic state, space derivatives of the density and fluctuations of physical quantities; and causing the computer to compute the exact solution, in a space being composed of a set including a plurality of groups as elements, each group being comprised of a model Hamiltonian decided when the energy functional is introduced and the order parameter deciding the electronic state, by generating the elements, based on whether a distance between the elements meets a given convergence, comprising computing a distance between the elements using the order parameter with respect to the elements included in the set, if the distance between the groups meets the given convergence then generating the exact solution of the electron state of the crystal structure based on the elements and terminating, else computing the approximate value regarding a functional derivative of the energy functional, estimating an asymptotic direction toward the exact solution from approximate values of functional derivatives of the energy functional, incrementing the order parameter of the respective model Hamiltonians of the groups, based at least in part on the estimated asymptotic direction, and repeating the generating the elements.

9. The non-transitory computer-readable recording medium of claim 8 wherein the deviation is a residual exchange-correlation energy functional.

* * * * *